United States Patent
Wang et al.

(10) Patent No.: US 9,315,078 B2
(45) Date of Patent: Apr. 19, 2016

(54) REAL-TIME WIRELESS DYNAMIC TIRE PRESSURE SENSOR AND ENERGY HARVESTING SYSTEM

(71) Applicant: Northeastern University, Boston, MA (US)

(72) Inventors: Ming Wang, Melrose, MA (US); Qi Wang, Malden, MA (US); J. Gregory McDaniel, Lexington, MA (US); Nian X. Sun, Winchester, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 14/084,156

(22) Filed: Nov. 19, 2013

(65) Prior Publication Data

US 2014/0070935 A1   Mar. 13, 2014

Related U.S. Application Data

(63) Continuation of application No. PCT/US2012/038842, filed on May 21, 2012.

(60) Provisional application No. 61/488,399, filed on May 20, 2011, provisional application No. 61/448,407, filed on May 20, 2011.

(51) Int. Cl.
*B60C 23/02* (2006.01)
*B60C 23/04* (2006.01)
(Continued)

(52) U.S. Cl.
CPC ........... *B60C 23/041* (2013.01); *B60C 23/0469* (2013.01); *B60C 23/0486* (2013.01);
(Continued)

(58) Field of Classification Search
CPC .............................................. B60R 2021/01308
USPC ......... 340/442, 443, 445, 447; 73/146, 146.5; 701/31.9, 33.7, 34.4, 37; 303/140, 146; 290/1 A, 1 R
See application file for complete search history.

(56) References Cited

U.S. PATENT DOCUMENTS 2,966,650 A   12/1960   Earnest
4,356,591 A   11/1982   Lude
(Continued)

OTHER PUBLICATIONS

International Search Report and Written Opinion issued by the U.S. Patent and Trademark Office as the International Searching Authority for International Application No. PCT/US2012/038842 mailed Jan. 28, 2013 (15 pgs.).

*Primary Examiner* — Van Trieu
(74) *Attorney, Agent, or Firm* — Wilmer Cutler Pickering Hale and Dorr LLP

(57) ABSTRACT

An instantaneous/real-time wireless dynamic tire pressure sensor (DTPS) for characterizing pavement qualities and for detecting surface and subsurface pavement defects under normal driving conditions. Signal processing provides quantitative assessment of surface conditions. DTPS includes a vehicle tire valve stem-mounted pressure sensor and wheel hub-mounted signal conditioning, amplification, and transmitting circuitry. A signal processing computer within the vehicle is wirelessly coupled to the hub-mounted circuitry. Tire pressure changes caused by ground vibration excitation from the interaction between the tire and pavement at normal driving speeds are detected. When acoustic radiation from a surface wave is significantly stronger than acoustic noise, subsurface information can be extracted. An energy harvester based on strong magnetostatic coupling between a high permeability core solenoid, fixed proximate a vehicle wheel, and a bias magnet array, fixedly mounted in conjunction with a dust shield, can provide power the DIPS.

28 Claims, 12 Drawing Sheets

(51) Int. Cl.
  *B60W 40/06* (2012.01)
  *B60R 21/013* (2006.01)

(52) U.S. Cl.
  CPC ...... *B60W40/06* (2013.01); *B60R 2021/01304* (2013.01); *B60R 2021/01306* (2013.01); *B60R 2021/01308* (2013.01)

(56) References Cited

U.S. PATENT DOCUMENTS

| | | | |
|---|---|---|---|
| 6,060,984 A | 5/2000 | Braun et al. | |
| 6,474,832 B2 * | 11/2002 | Murray | 362/192 |
| 6,591,668 B1 * | 7/2003 | Becherer et al. | 73/146 |
| 7,036,616 B1 | 5/2006 | Kejha | |
| 7,102,244 B2 | 9/2006 | Hunter, Jr. | |
| 7,116,036 B2 | 10/2006 | Balasubramaniam et al. | |
| 7,248,054 B2 | 7/2007 | Kalokitis et al. | |
| 7,562,563 B2 | 7/2009 | Wee | |
| 2003/0005759 A1 * | 1/2003 | Breed et al. | 73/146 |
| 2005/0065711 A1 | 3/2005 | Dahlgren et al. | |
| 2006/0022555 A1 | 2/2006 | Balasubramaniam et al. | |
| 2007/0279204 A1 * | 12/2007 | Adar et al. | 340/447 |
| 2008/0243327 A1 * | 10/2008 | Bujak et al. | 701/29 |
| 2008/0243334 A1 * | 10/2008 | Bujak et al. | 701/37 |
| 2009/0088896 A1 * | 4/2009 | Tobey | 700/245 |
| 2009/0308657 A1 | 12/2009 | Clark et al. | |
| 2010/0176604 A1 * | 7/2010 | Bravo | 290/1 R |
| 2010/0289271 A1 | 11/2010 | DiMauro et al. | |
| 2011/0000596 A1 * | 1/2011 | Sachdev et al. | 152/339.1 |

* cited by examiner

REAL-TIME WIRELESS DYNAMIC TIRE PRESSURE SENSOR AND ENERGY HARVESTING SYSTEM

CROSS REFERENCE TO RELATED APPLICATIONS

This application claims priority to and is a continuation of International Application No. PCT/US2012/038842 filed May 21, 2012, entitled "REAL-TIME WIRELESS DYNAMIC TIRE PRESSURE SENSOR AND ENERGY HARVESTING SYSTEM," which claims the priority of U.S. Provisional Application No. 61/488,399 filed May 20, 2011, entitled "REAL-TIME WIRELESS DYNAMIC TIRE PRESSURE SENSOR (DTPS)," and U.S. Provisional Patent Application No. 61/488,407 filed May 20, 2011, entitled "WIRELESS ENERGY HARVESTING SYSTEM FOR REAL-TIME PRESSURE MONITORING SYSTEM." The aforementioned related applications are hereby incorporated by reference in their entirety.

STATEMENT REGARDING FEDERALLY SPONSORED RESEARCH OR DEVELOPMENT

The research leading to this invention was carried out with U.S. Government support provided under a grant from the National Institute of Standards and Technology (NIST) Technology Innovation Program (TIP), Grant No. 70NANB9H9012. The U.S. Government has certain rights in the invention.

BACKGROUND OF THE INVENTION

Various sensor systems widely are used in inspecting the nation's infrastructure of roads and bridges. Unfortunately, infrastructure integrity cannot be conveniently evaluated in an economically or time efficient way using these existing systems. Techniques using acoustic microphones, accelerometers and geophones have been proposed to meet the increasing demands for integrity evaluation and to prevent significant and potentially irreversible infrastructure degradation.

It has been widely recognized that the propagation of surface acoustic waves through concrete/asphalt layers can be measured by accelerometers or microphones; the propagation characteristics can be used to assess/estimate the material and structural properties, including the existence of damage in the surface and sub-surface of the structure. Static systems relying upon an external impact source to produce acoustic signals measureable with an acoustic transducer or an array of acoustic transducers are considered an effective way for surface and subsurface sensing.

One acoustic wave-based method for detecting the subsurface pavement profile is the air-coupled surface wave measurement using multichannel analysis of surface wave (MASW) technique. A microphone array is suspended in the air, close to the ground, to collect leaky surface waves excited by a nearby hammer impact. In the time domain, the surface wave can be separated from the direct hammer noise in subsequent data processing. After the whole set of tests are finished, an iterative dispersion analysis, relying upon manual experience and intervention, is executed in order to achieve the estimation of subsurface profile. However, the data analysis is sensitive to the interference of ambient noise and hammer noise. The manipulation from test point to test point is rather slow. Besides, an external impact excitation is not capable of measuring the surface condition.

There is a significant need for a time-efficient inspection system with an automatic excitation source. Tire and road surface interaction produces acoustic signals, and these signals are measureable with an acoustic transducer or an array of acoustic transducers. Specifically, using the tire as a mechanical excitation source eliminates the need for external impact used in previous sensor systems. Roadway surface vibrations, circumferential tire vibrations and air pressure vibrations are generated as the tire rolls over the surface of asphalt, concrete or other roadway surface. The vibrations travel as surface waves on the road and through the rubber of the tire and propagate through the air with volumetric attenuation. Acoustic waves are affected by the material and structural properties of the volume through which they propagate; therefore, by the accurate recording of acoustic wave signals and necessary signal processing, one can characterize the structural and material properties of a surface.

The current method for monitoring the static tire pressure and its change over time is the tire-pressure monitoring system (TPMS) deployed in many modern cars. This system was originally designed to identify under-inflation in any of the four tires of the vehicle. With TPMS, direct tire pressure sensors are mounted inside each tire to measure the static pressure every 30 seconds, and the information is wirelessly transmitted to the vehicle's instrument cluster. The sole purpose of the TPMS is to obtain the tire pressure and provide a low-pressure warning to the vehicle; therefore it does not provide a high sampling rate for tire pressure change, high transmitting rate, or an indication of dynamic tire pressure.

Due to a critical power requirement of electronic sensor nodes and wireless sensor networks, such as the TPMS, normal batteries are not durable enough and they typically increase size and weight of the sensor nodes. They also impose the maintenance burden of power recharging or replacement. Therefore, various energy harvesting technologies have been proposed for converting mechanical energy into electricity as an option for renewable power. Energy sources including mechanical motion, wind, ocean surface waves, and ambient vibrations have gained attention as novel green energy alternatives for powering electronic sensors.

As one of the most popular energy harvesting methods, harvesting vibration energy in either on- or off-resonance mode has been applied for wireless sensor networks and infrastructure health monitoring systems. A piezoelectric material acting as a transducer has been used in vibration energy harvesting systems, and optimum mechanical structures have been studied. These systems are usually lightweight and small in size. However, the major disadvantages of these vibration energy harvesting methods include: 1) the ambient vibration energy that the harvester can use is tiny; 2) these devices are limited/tuned for operating on single or narrow operating frequencies, thus it is impossible to adopt the same design for different applications; and 3) the overall output energy for various designs is in $\mu W$ to mW range, which is insufficient for any critical instantaneous/real-time sensor network application.

Mechanical motion has been proposed as another energy harvesting method, in which energy from relative motion between an oscillating proof mass and a frame structure that is harvested. One example is harvesting kinetic energy from human working or other motion; a spring and piezoelectric material are usually used to support a proof mass in such design. However, this type of energy harvester shares the same three disadvantages as mentioned earlier for the vibration energy harvesting methods. Further, this intermittent human motion energy source is not available all the time which limits its power generation and storage capability for critical sensor node applications.

Another example is harvesting rotating kinetic energy from rotating structures based on a conventional DC motor. These DC motor based designs consist of a well-designed load mass as a gravitational torque generator, whose natural frequency is close to the rotating wheel frequency, and a rotational source on- or off-axis of the rotation of a host wheel. The amount of drag torque and tensile stress due to centrifugal force in a radial orientation depends on the speed.

The latter class of device has been tested on an instrumented rotating structure/wheel in a lab setting but are not believed to have been implemented on an actual vehicle wheel. Therefore, energy harvested by such a system cannot be used by conventional electrical sensors near a tire or within a vehicle. Further, their fixed or narrow working bandwidth and their low power density output range limits their utility in an actual vehicle.

BRIEF SUMMARY OF THE INVENTION

Disclosed is a non-destructive and non-contact acoustic sensing technique, including method of use and apparatus therefor, for fast inspection of road and bridge deck conditions with vehicles running at normal speed without the need for delaying or stopping other traffic. Such a sensing technique and platform possesses certain advantages, such as enabling non-destructive testing, not requiring periodic, striking contact, enabling travelling sensors, and not requiring the interruption of normal driving patterns. The disclosed approach, which uses a real-time Dynamic Tire Pressure Sensor (DIPS), possesses the capability to inspect pavement conditions from a moving vehicle.

Verification of the DIPS concept of sensing inside the tire has been carried out. By measuring dynamic pressure change inside the tire, ground motion can be amplified and isolated from environmental noise. A prototype real-time DIPS with wireless system has been developed and demonstrated on a van at speeds from 10 to 60 miles per hour (mph). A data analysis algorithm has been developed and optimized to enhance detection accuracy. Numerical and experimental studies of this real-time wireless DIPS (above 30 kHz) reveal the potential for using tire generated acoustic signals to detect the condition of bridge deck and road pavement in the frequency range between 30 Hz to 15 kHz.

The transducer or transducers for prior proposed methods and systems needed to be placed close to the tire and suspended close to the ground on a traveling vehicle. Aside from the obvious risk of transducer impact with the ground, there is a risk that the ambient noise would prevent the detection of acoustic signals from the tire-road interface and surface waves that propagate in the road. Moreover, for most cases, sophisticated signal processing methods are typically required in such analysis.

In contrast, the disclosed approach places a dynamic tire pressure sensor inside the tire. Specifically, a real-time dynamic tire pressure sensor (DIPS) has been developed. New hardware components and associated supporting signal processing strategies that provide an assessment of both surface and subsurface conditions have been evaluated. Due to the rotating tire, a wireless transmission system is also developed and evaluated for real-time DIPS on a testing van with a wide range of driving speeds, including highway speeds. Other speeds may also be achievable. Unique features of DTPS include: the tire is able to act as a natural barrier to external noise; the tire is directly in contact with the ground; the instruments are protected from the environment; samples are taken in real-time; surface characteristics and subsurface debonding or other defects can be detected; and, in conjunction with geo-locating devices such as a Global Positioning System (GPS) receiver, roadway condition information can be mapped with precision. Still images and/or video of the roadway and/or immediate environment may also be associated with or integrated into the processed DIPS data to enable the later location of any pavement portions requiring maintenance.

The advantages of DIPS over former approaches, such as static measurement of a ground wave using plural, fixed accelerometers, plural fixed directional microphones, are as follows: dynamic pressure is measured, instead of static pressure; testing can be performed while the vehicle is moving, as opposed to fixed testing; an instant/real-time pavement condition report is generated instead of an in-office, post-test report; the instrumented tire allows for fast, continuous testing, as opposed to slow testing due to frequent sensor mounting and removal; and it is suitable for thorough inspection of an entire pavement length. Depending upon data transmission requirements, the DIPS can be wireless or wired.

Both surface and subsurface defects have been studied using DIPS under different conditions, such as various speeds and defect magnitudes, different background noise, and working frequency bands of DIPS. The wireless communication transmitter wirelessly reports data from the dynamic tire pressure sensor to an onboard processor where data is processed and any potential road defect triggers are reported to a central database. The DTPS system gives real-time and networked information about the state of the pavement surface and subsurface, which is highly desired.

Data for assessment analysis at operational speeds such as 60 mph is thus gathered without congesting traffic. Data registration methods have also been developed for accurate, geo-referenced positioning information with decimeter resolution. Data registration determines the precise location associated with each instance of collected data and features required for a high-resolution geophysical subsurface imaging operation on a mobile platform. The DIPS data collected is preferably time-stamped by a clock synchronized to the clock of the positioning system, which allows people to dereference all DIPS data.

Also disclosed herein is a rotating energy harvester that can power electronic sensors and wireless sensor networks, such as found in conjunction with a TPMS or the presently disclosed DIPS. This energy harvester design is based on magnetostatic coupling between a stationary circular-arc hard magnet array and rotating magnetic solenoids consisting of a unique core with high permeability (>10,000 H/m) for significantly increasing the output power density. The hard magnet array consists of magnets with anti-magnetization producing a spatially heterogeneous bias magnetic field, which switches the flux inside the solenoids during relative motion between the magnet array and the magnetic solenoids. A prototype of this rotating energy harvesting system has been fabricated and demonstrated on a rotating wheel at speeds from 10 to 60 miles/hour (mph). Results of different rotating frequencies show average power densities from 1 to 5 W/cm$^3$. Comparisons of different magnetic solenoids as well as different energy storage circuits have been carried out. A numerical and experimental study of powering a real-time wireless tire pressure monitoring system (TPMS) reveals that the energy harvester design generates constant and steady power sufficient for continuous operation of the TPMS. This leads to the conclusion that the energy harvester has applicability to other wirelessly-communicating sensors.

BRIEF DESCRIPTION OF THE SEVERAL
VIEWS OF THE DRAWINGS

The foregoing and other objects, features, and advantages of the invention will be apparent from the following description of embodiments of the invention, as illustrated in the accompanying drawings in which like reference characters refer to the same parts throughout the different views. The drawings are not necessarily to scale, emphasis instead being placed upon illustrating the principles of the invention.

Figure 4:
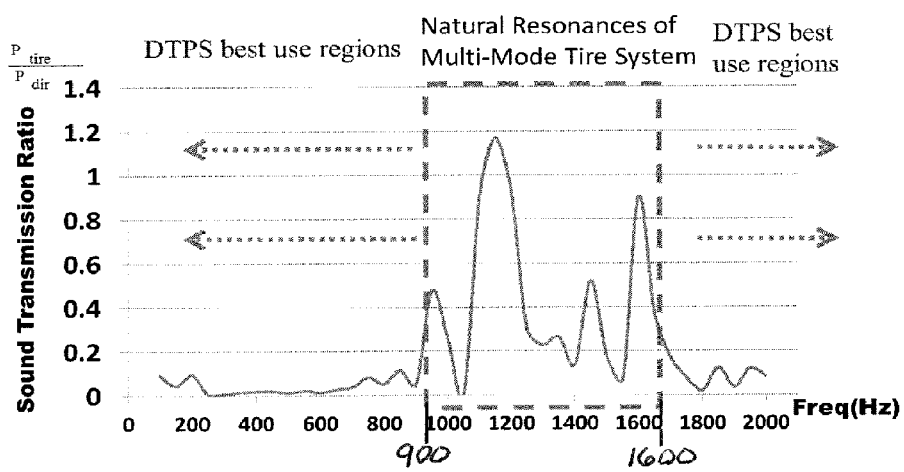
FIG. 4 is a graph of a sound transmission ratio or transfer function into a tire wall ($P_{tire}/P_{dir}$) versus the frequency of an externally applied test tone.
Figure 6:
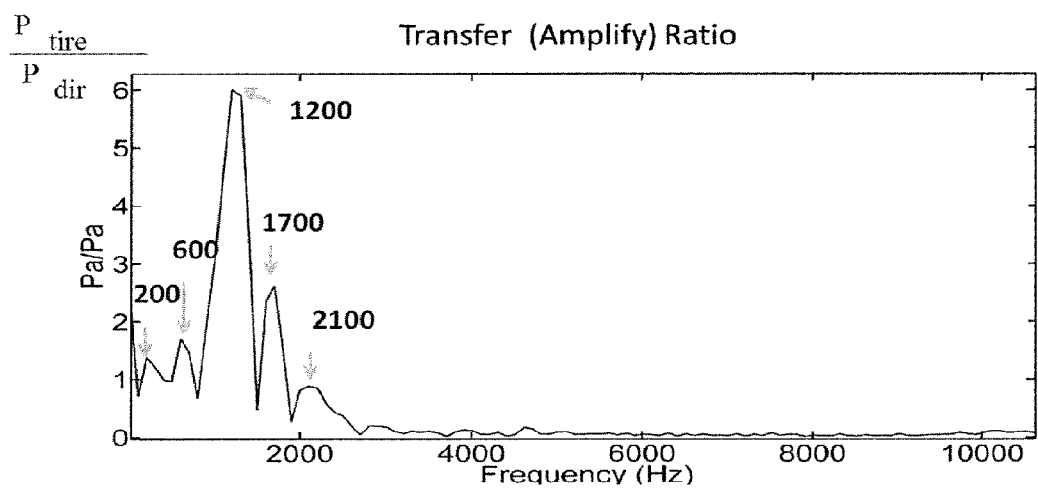
Figure 7:
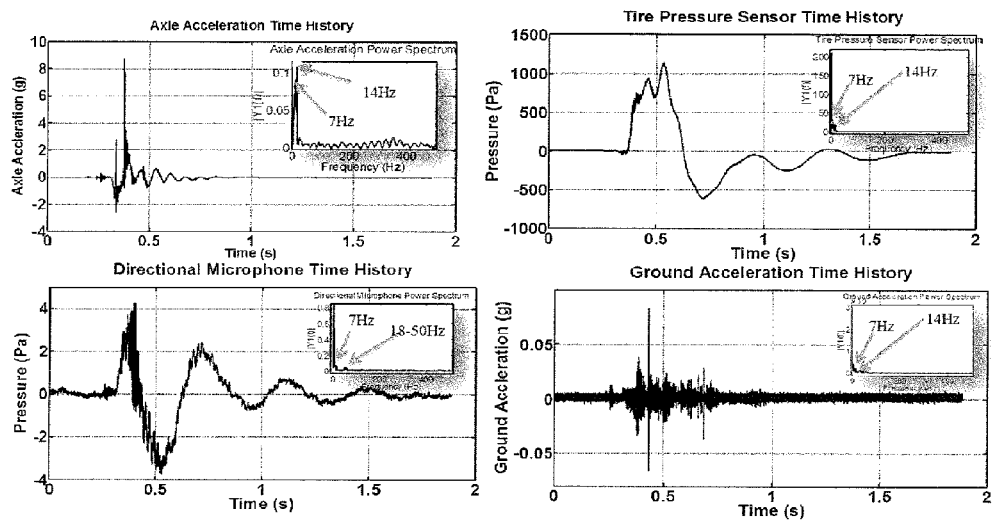
Figure 8:
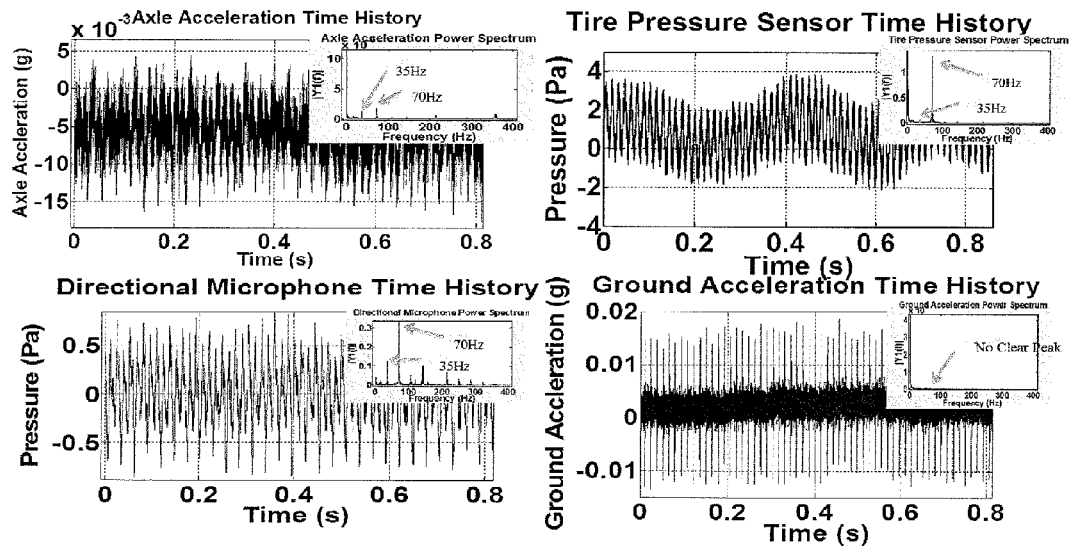
Figure 9:
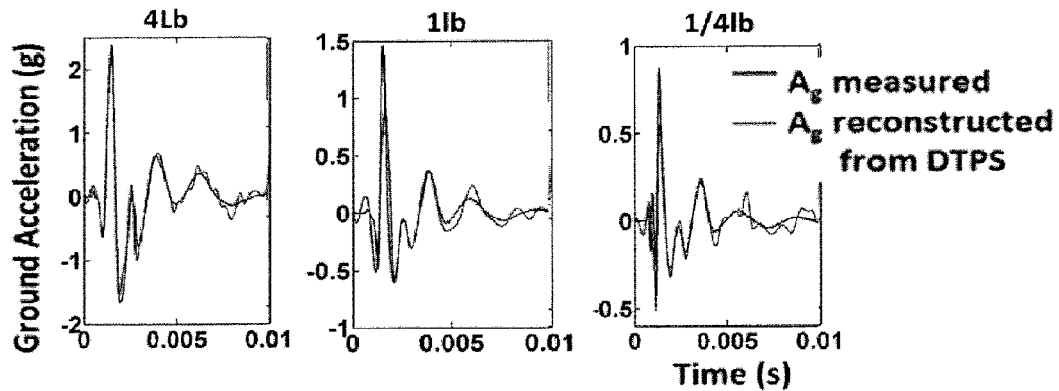
Figure 10:
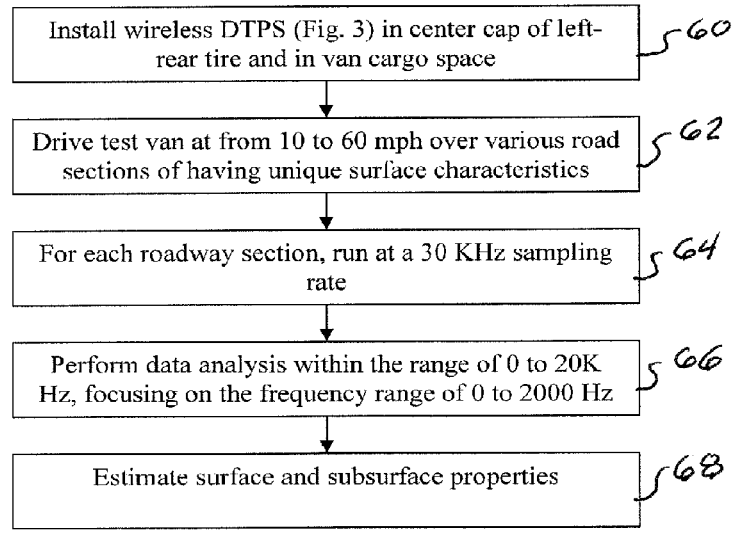
Figure 11:
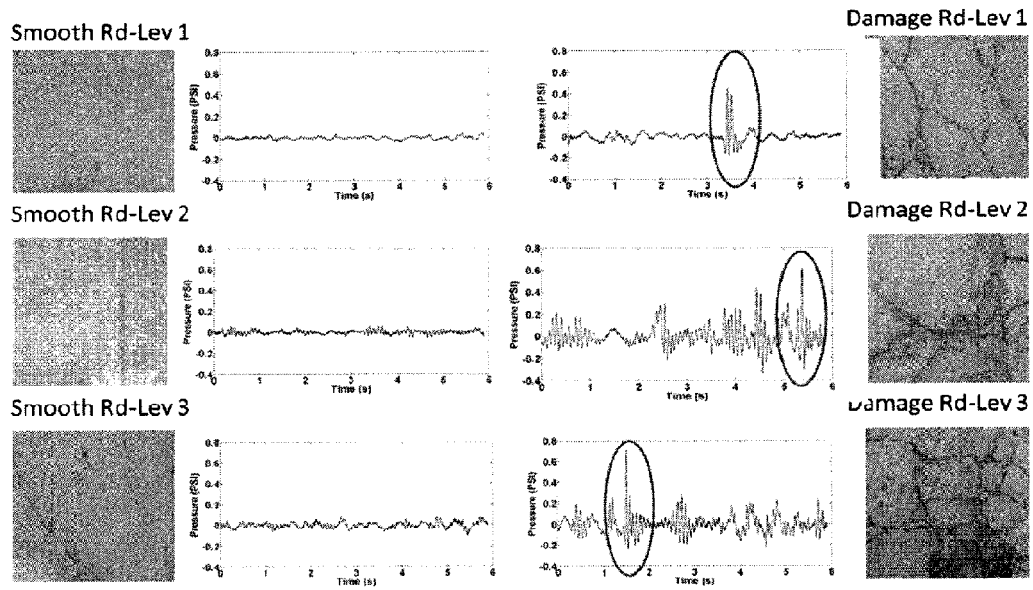
Figure 12:
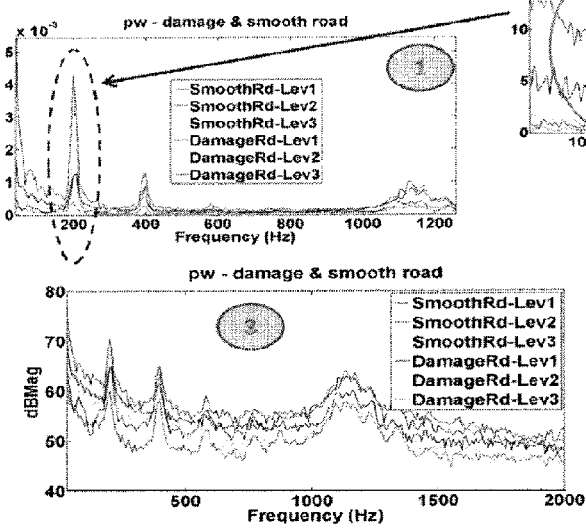
Figure 12:
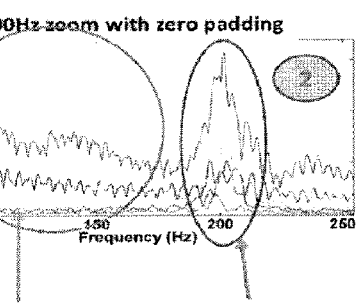
Figure 13:
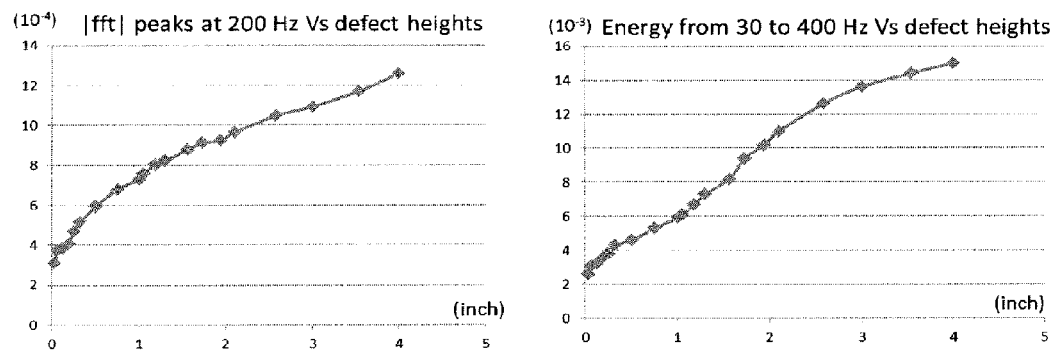
Figure 14:
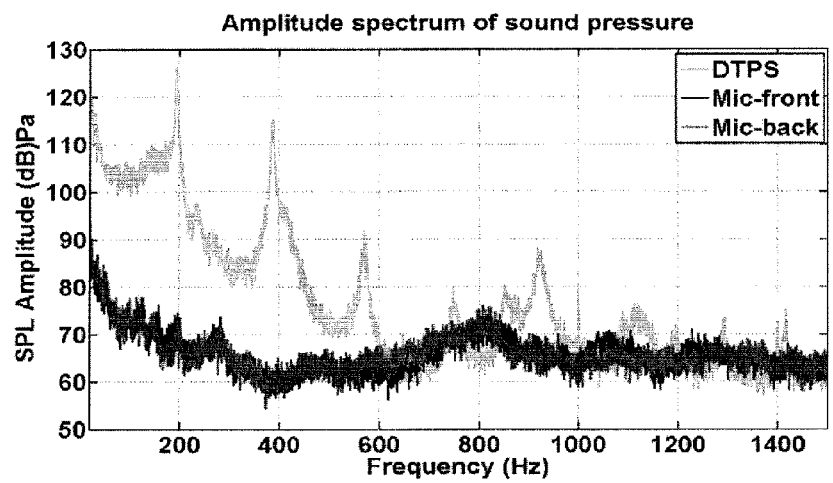
Figure 15:
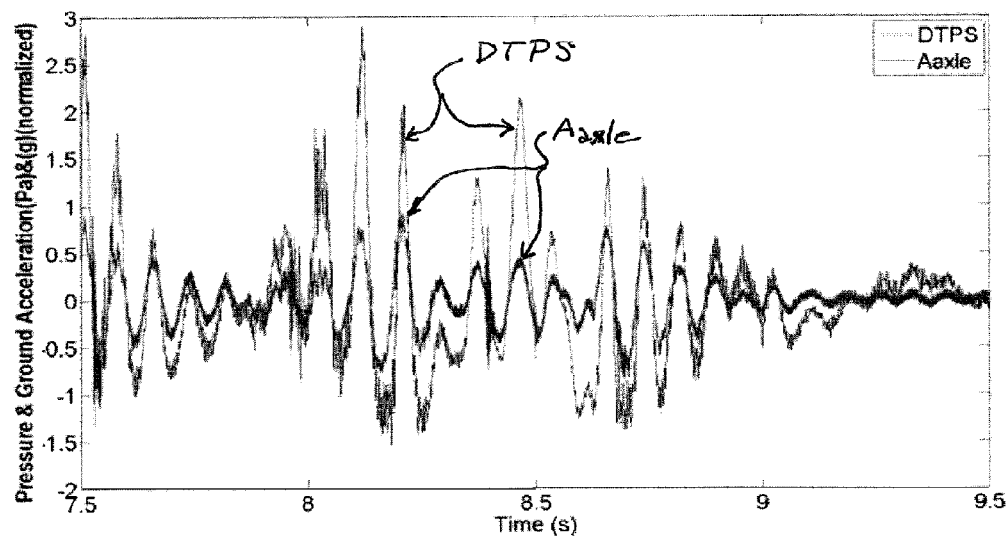
Figure 16:
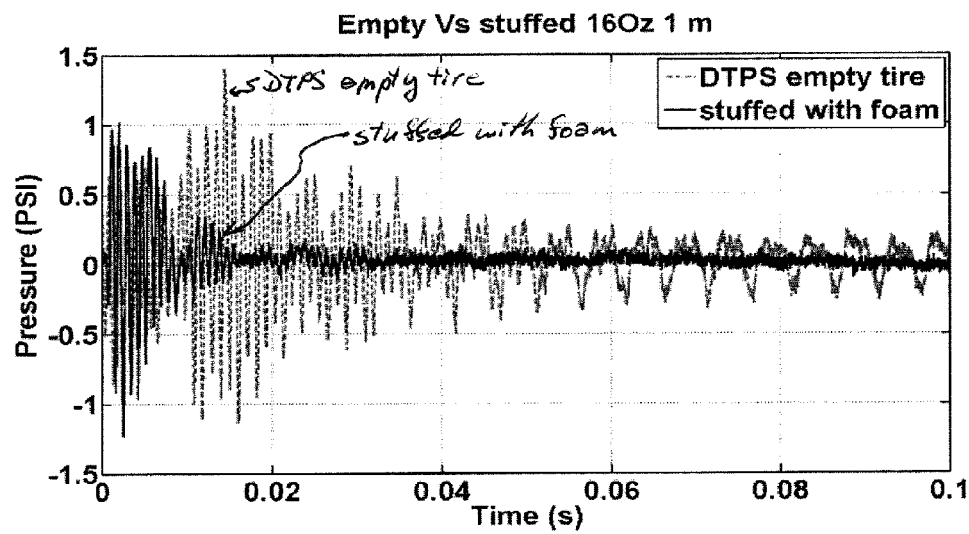
Figure 17:
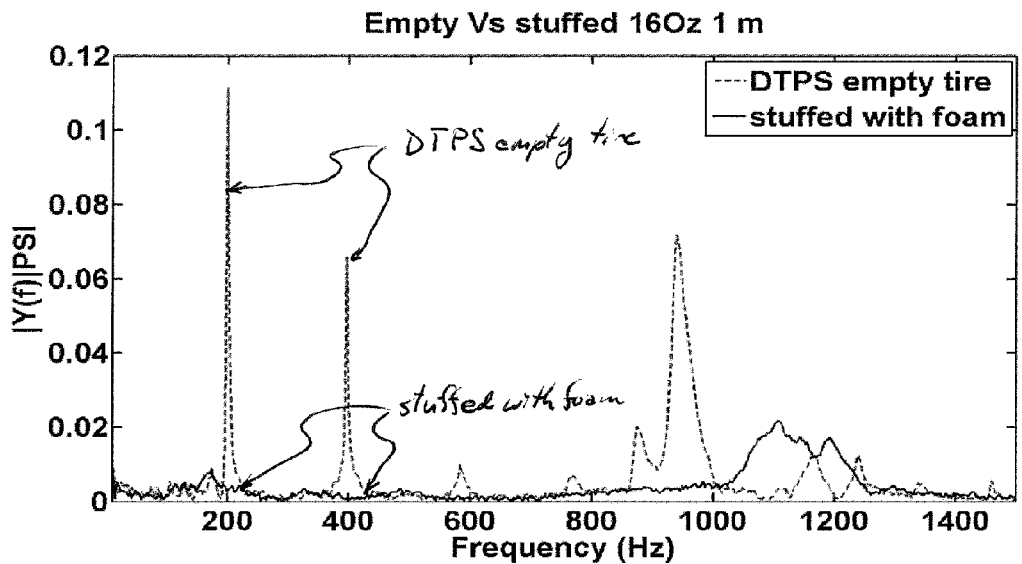
Figure 18:
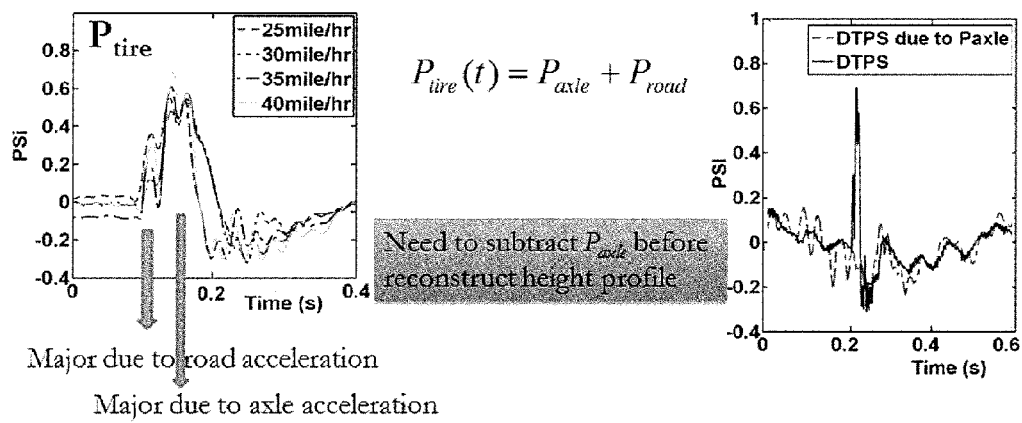
Figure 19:
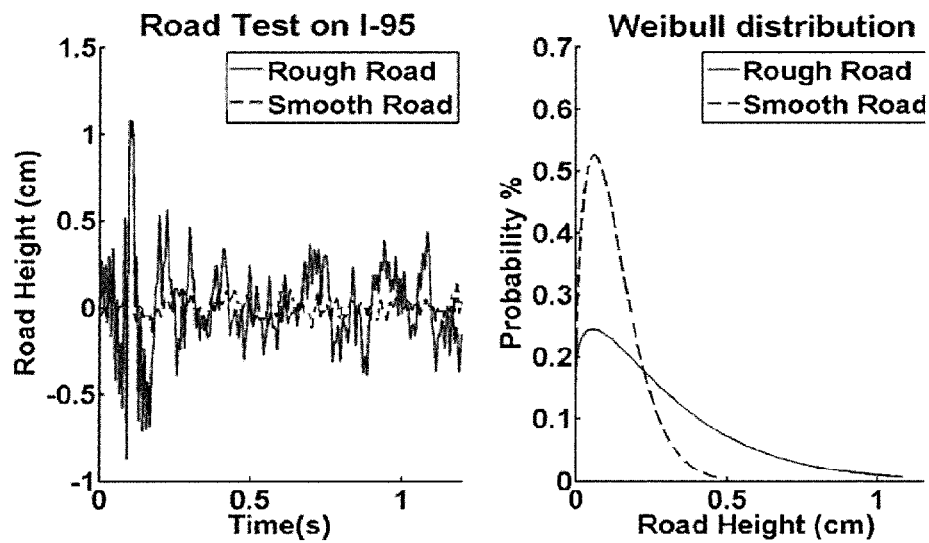
Figure 20:
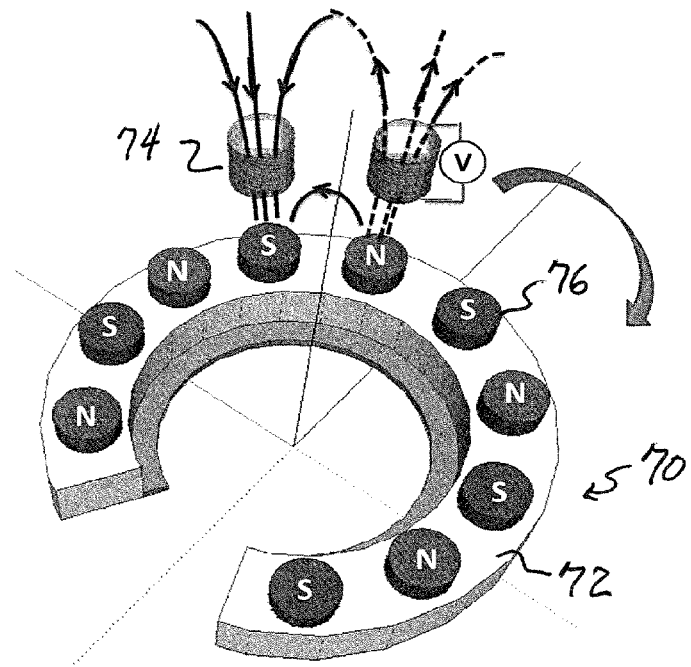
Figure 21:
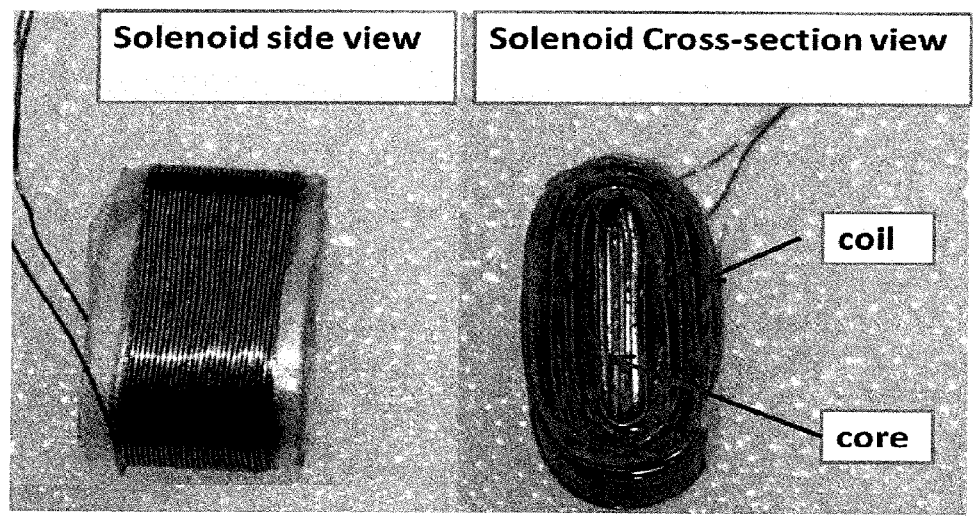
Figure 22:
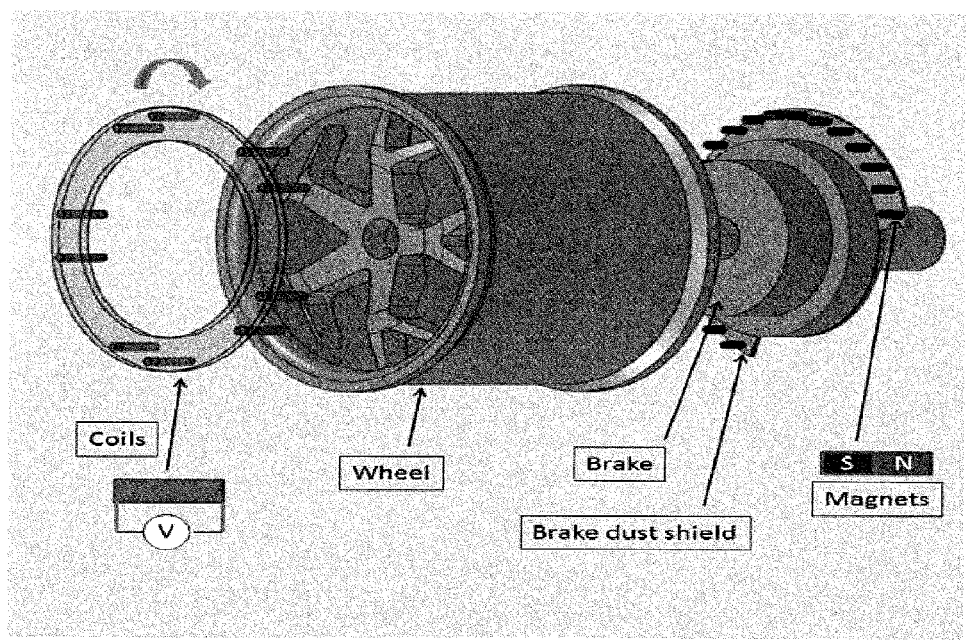
Figure 23:
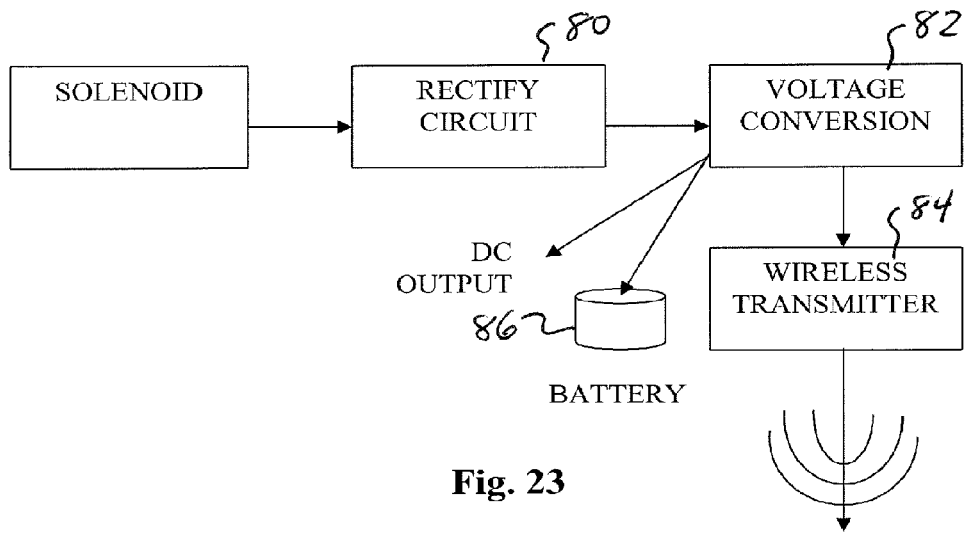
Figure 24:
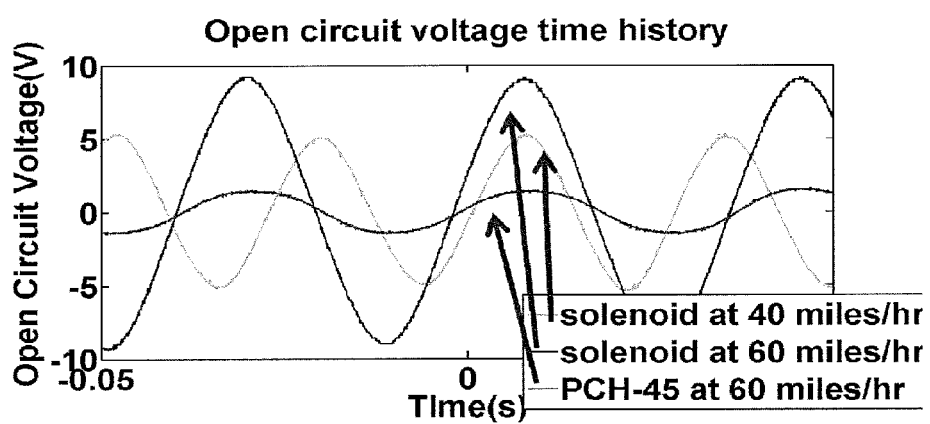

FIG. 6 includes a graph of the transfer function of FIG. 4 versus frequency;

FIG. 7 includes graphs of the response of an axle-mounted accelerometer, a directional microphone, the DIPS, and a ground-mounted accelerometer to a single low-frequency impact in the time domain;

FIG. 8 includes graphs of the response of the sensors of FIG. 7 to a continuous high-frequency impact in the time domain;

FIG. 9 includes graphs of measured accelerometer response versus accelerometer response derived from DIPS data for each of three different hammer strikes;

FIG. 10 is a flow chart of how the wireless DTPS is installed and used for roadway characterization;

FIG. 11 includes graphs of the DIPS response in the time domain for each of six types of roadway features and including a photograph of a portion of each roadway;

FIG. 12 includes graphs of a frequency analysis for the DIPS results in FIG. 11;

FIG. 13 includes graphs depicting the relationship between roadway defect heights and frequency analysis of the DIPS results;

FIG. 14 includes a graph depicting the sound pressure amplitude spectrum for DIPS and two directional microphones, one mounted outside the vehicle and in front of the DIPS-mounted tire/wheel and another mounted outside the vehicle and behind the DIPS-mounted tire/wheel;

FIG. 15 includes a graph depicting the response of the DIPS and an axle-mounted accelerometer to the respective vehicle being driven over a portion of pavement;

FIG. 16 includes a graph depicting the response of the DIPS in time to a vehicle striking a roadway obstacle without and with acoustic damping material in the respective tire;

FIG. 17 includes a graph depicting the response of the DIPS in frequency to a vehicle striking a roadway obstacle without and with acoustic damping material in the respective tire;

FIG. 18 includes graphs depicting the response of the DIPS in time to a vehicle striking a roadway obstacle at various speeds, and the derived pressure attributable to axle acceleration;

FIG. 19 includes graphs depicting roadway height profiles derived from DTPS data;

FIG. 20 depicts an arcuate magnet array for use in an energy harvester capable of powering the DIPS according to the present disclosure;

FIG. 21 depicts a solenoid/coil used in the energy harvester according to the present disclosure;

FIG. 22 depicts the arrangement of the magnet array of FIG. 20 mounted on a vehicle brake dust shield and plural solenoids/coils of FIG. 21 disposed in conjunction with a vehicle wheel;

FIG. 23 is a block diagram of a portion of the energy harvester according to the present disclosure; and FIG. 24 is a graph of the open circuit AC voltage of the energy harvester according to the present disclosure generated at various simulated vehicle speeds.

DETAILED DESCRIPTION OF THE INVENTION

Different acoustic and surface waves are generated at specific frequencies and amplitudes while a vehicle is traveling on varying road surfaces. These waves depend in part on the material properties of the road structure. The atmospheric acoustic field between the vehicle chassis and the road is also complex. Acoustic sources include aerodynamic effects, vehicle body vibration, ground vibration, direct radiation from the tire-road interface, and ambient noise due to other vehicles or acoustic sources.

Specifically, there are five distinct wave types that can be coupled to form acoustic waves within a subject vehicle tire due to complex interactions of the tire with the road surface. These different effects on the tire are: 1) direct surface wave from other tires or vehicles passing on the roadway nearby; 2) the acoustic wave from the interaction of the subject tire rolling on the roadway; 3) tire vibration (elastic) from, for example, axle vibration, or own tire excitation; 4) under chassis, body-ground wave, generated by radiation from the respective vehicle; and 5) ambient noise, such as wind noise, engine noise, etc.

Tire inflation pressure supports the structure of the tire and the weight of the vehicle as it travels along a road. Any disturbance at the tire-pavement interface such as a bump in the pavement will cause minor compressions and expansions of the tire walls, dynamically changing the tire internal pressure. By sensing the dynamic pressure change, instead of measuring static or quasi-static pressure as practiced in the art, ground motion can be amplified and isolated from environmental noise inside the tire.

With the real-time Dynamic Tire Pressure Sensor (DTPS) technique, the tire acts as a tube cavity having its own resonance frequency. An approximate equation for the first natural frequency is given as $$f = \frac{c}{l} = \frac{2c}{\pi(D+d)} [\text{Hz}], \quad (1)$$

where c is the speed of sound in the gas inflating the tire, l is length of the tire cavity, D is outer diameter of the cavity and d is inner diameter of the cavity. The cavity resonance is defined by the tire and rim size as well as the speed of sound in the acoustic medium that inflates the tire. Knowing tire cavity resonance frequency is helpful in locating the desired ground motion characteristics during data analysis. Compared to sensing acoustic signals outside of the tire, the DTPS signal can be quantified precisely as:

$$P_{int} = G\left(\frac{P_{int}}{P_{ext}}\right)P_{ext} + G\left(\frac{P_{int}}{V_g}\right)V_g, \quad (2)$$

where, $P_{int}$ is the interior pressure, $G(P_{int}/P_{ext})$ is the transfer function of interior pressure to exterior pressure, and $V_g$ is ground vibration. The transfer function of $G(P_{int}/P_{ext})$ can be estimated based on the following experiment performed with and without the ground vibration input ($V_g$) term. From equation (2), it is seen that the interior pressure measured by DTPS is comprised of a first input resulting from external noise and a second input resulting from ground vibration/acceleration.

An initial experiment was carried out to assess the capability of DIPS to act as an external noise barrier. Thus, this test is an attempt to quantify the first input in equation (2). A Chevrolet Express 3500 cargo van with tire 10 model LT245/75R16E was used as testing platform. Ground vibration $V_g$ was excluded by suspending the tire from the ceiling of a laboratory. An omnidirectional electret condenser microphone 12 (Sony ECM-55B) and a dynamic pressure sensor 14 (PCB Piezotronics 106B52) were connected to an acoustical signal acquisition unit 16 (Data Physics Quattro). Processing of the acquisition output is handled by a personal computer 22 (PC). The test configuration is diagrammed in FIG. 1. Pure tones were generated from 50 to 2000 Hz at 50 Hz intervals using a laptop (not shown) and a speaker 20 a distance of one half meter from the DIPS and microphone. The results of this analysis are provided below.

Figure 2:
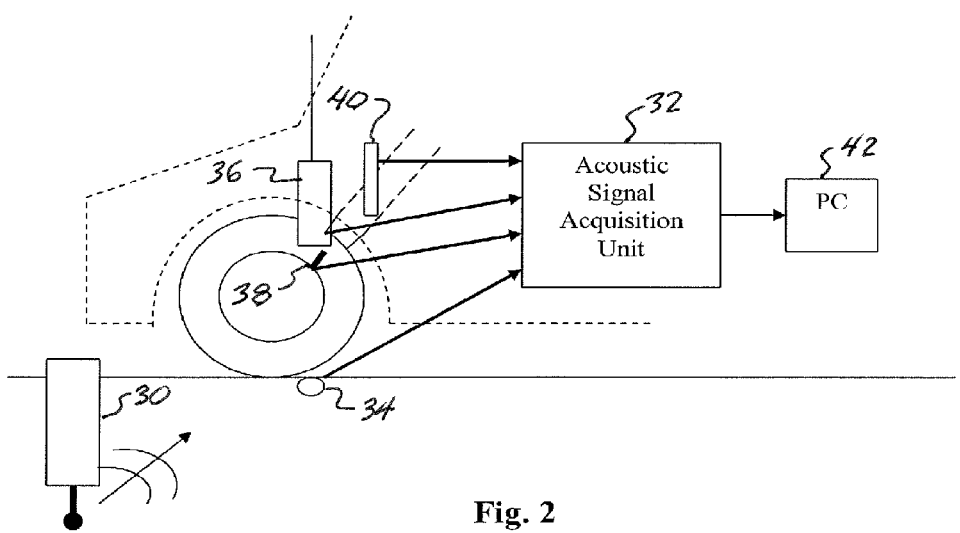
FIG. 2 is a block diagram of a test configuration used to characterize the ability of the DIPS of FIG. 3 to amplify ground vibration.

In order to assess the capability of DIPS as a ground vibration/acceleration amplifier, four sensors were used with the test van. A stationary test was performed with an external impact source 30 (Kistler Force Hammer, 1 lb) at a distance of one meter from the tire/road surface contact point. FIG. 2 illustrates the test configuration. An acoustical signal acquisition unit 32 (Data Physics Quattro), connected to a signal processing computer 42, was used for the four channels, which were: 1) an accelerometer 34 (Bruel & Kjaer Accelerometer 4507B004) mounted on the ground one inch from tire/road contact point; 2) a directional microphone 36 (G.R.A.S. Directional microphone 40AE) suspended in the air one inch away from value stem of the tire; 3) the DIPS 38 connected to the valve stem and including a DIPS adapter fabricated to enable tire inflation up to 75 Psi without damaging the DIPS; and 4) an accelerometer 40 (Bruel & Kjaer Accelerometer 4507B004) mounted on the axle of the test tire. The results of this analysis are discussed below.

In order to improve the response of the DIPS to surface vibrations, it was determined that acoustic response of the tire at resonance needed to be decreased. One approach to achieving this goal was through the installation of acoustic damping material, such as acoustic foam sheets with pyramidal projections, into the tire housing the DIPS.

Figure 5:
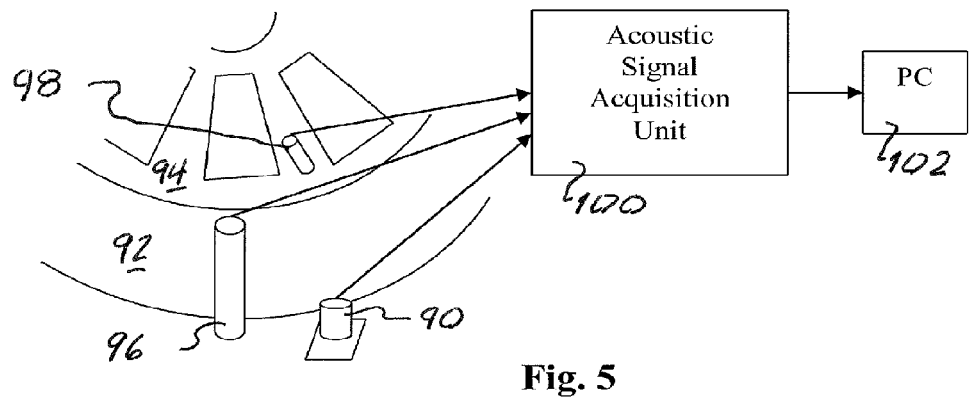
FIG. 5 is a block diagram of a further test configuration used to characterize the performance of the DIPS with respect to a directional microphone and a ground-mounted accelerometer.

A test configuration as shown in FIG. 5 was used to validate the use of the foam insert. A ground-mounted accelerometer 90 was disposed adjacent a stationary tire 92 and wheel 94. A DPTS 98 was mounted on the valve stem of the tire. A directional microphone 96 was suspended proximate the accelerometer. All three sensors were connected to an acoustic signal acquisition unit 100 that provided an output to a programmed personal computer (PC) 102. A 16 ounce hammer (not shown) impacted the pavement approximately one meter from the sensors. As is evident from the graphs of FIGS. 16 and 17, the DIPS without a foam liner installed in the tire exhibited a significant amount of resonant response compared to the case where the foam liner is installed.

Figure 3:
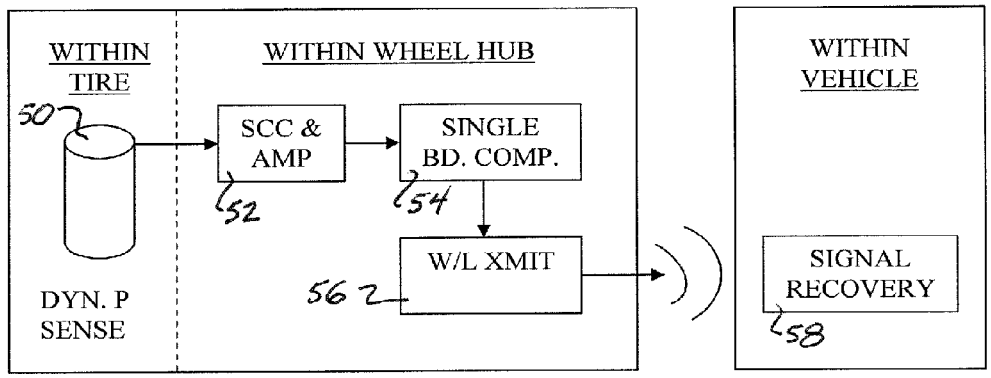
FIG. 3 is a block diagram of a wireless, real-time Dynamic Tire Pressure Sensor (DIPS) according to the present invention.

Building blocks of a wireless, real-time DIPS system disposed in conjunction with a vehicle tire are shown in FIG. 3 and consist of a dynamic pressure sensor 50 ("DYN. P SENSE"), a signal conditioning circuit 52 (Dataforth SCM5B48 input module) with amplifying circuit (lab fabricated) ("SCC & AMP") for receiving a data output from the pressure sensor, a single board computer 54 ("SINGLE BD. COMP.") including an eight-channel, twelve-bit analog-to-digital (A/D) converter (Technologic System TS-7250) for processing the pressure data from the conditioning unit, and a wireless transmitter 56 ("W/L XMIT") (Asus WL-167g WIFI-G-USB-2 dongle) for transmitting the processed data from the computer. Disposed within or on the vehicle itself is a signal recovery computer 58 ("SIGNAL RECOVERY") capable of receiving the transmission from the wireless transmitter and performing the necessary processing, data storage, and defect identification/alerting. The single board computer in one embodiment supports an optional eight channel, twelve-bit A/D converter (ADC) with a conversion time of 12 µS through the MAX 197 chip. This allows a sampling rate up to 60,000 Hz.

The signal recovery computer may also have stored in memory associated therewith a threshold value or set of threshold values. If the processed DIPS data exceeds one or more of these threshold values, it is assumed that degraded road conditions exist. The DTPS data may be flagged for easy subsequent identification. If a still or video camera is integrated into the DTPS system and is in communication with the signal recovery computer, one or more images may be captured upon threshold attainment to help locate the defective roadway. Further, the signal recovery computer may be programmed to issue an alert upon attainment of one or more threshold values. Such an alert may be an audible or visual signal to an operator or other personnel in the vehicle transporting the DIPS, or it may be a communication to remote personnel or a remote processor. Such an alert may include information related to the date, time, location and severity of the roadway defect.

In an experimental configuration, the DIPS was installed on the valve stem of the rear tire of the cargo van. The wireless system, comprised of the SCC, amplifier, single board computer, and transmitter, was assembled and disposed in the center cap or hub cover of the respective wheel. Preferably, the wireless system is provided in a weather-proof enclosure. Data was collected at a sampling rate of 30 kHz by the pressure transducer and was transmitted wirelessly to a signal recovery computer inside the same vehicle. The signal recovery computer processed the data and sent a report to a central database that may either be integrated therewith or remote, connected via suitable telemetry. This could be done continuously or upon detection of a triggering event such as identification of a potential road defect including a pothole, expansion joint, crack, bleed or corrugation.

In an alternative embodiment, particularly in the case where a larger data throughput between the DIPS and a data processing computer is required, a wired connection can be implemented. Thus, in FIG. 3, the wireless transmitter 56 becomes a wired transmitter or data driver connected to a data cable or cables via a hub-mounted slip ring. The wired connection allows for higher sampling rates (for example, 200 KHz) and synchronization of the DIPS with other sensors on the test vehicle, such as one or more vehicle body-mounted accelerometer, an axle-mounted accelerometer, one or more directional microphones, etc. This is discussed in further detail below.

An energy harvesting system, such as described below, was also assembled with respect to the tire dust shield for powering the real-time data collection and wireless transmission equipment.

Figure 1:
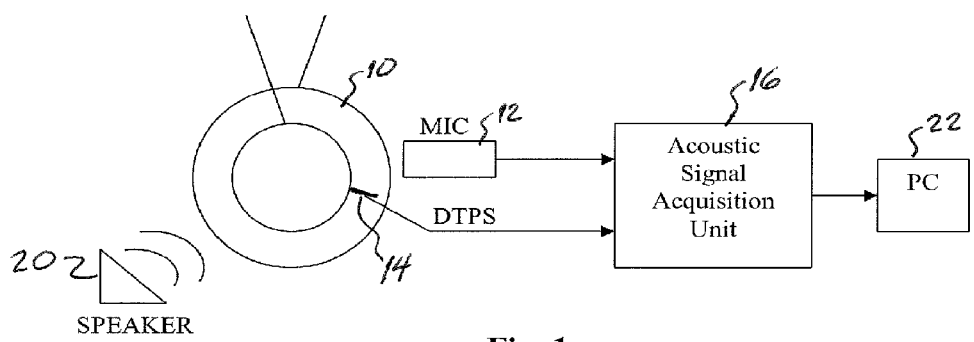
FIG. 1 is a block diagram of a test configuration used to characterize the ability of the Dynamic Tire Pressure Sensor (DIPS) of FIG. 3 to act as an external noise barrier.

A test, using the arrangement depicted in FIG. 1, was performed to determine whether the DTPS was sensitive to noise outside the tire. Stated differently, the test was performed to quantify the degree to which the overall interior pressure $P_{int}$ of equation (2) was affected by external noise. External noise over a range of frequencies was sensed inside the tire, with the goal of identifying the best working frequency range of the DTPS. A SignalCalc Dynamic Signal Analyzer and Matlab were used to analyze signals from the testing setup discussed above.

Initially, a sinusoidal pure tone input of 550 Hz was studied. In the time domain, peak to peak values of approximately 10 Pa were detected using a directional microphone 12. The peak to peak values for the DIPS 14 were approximately 1 Pa. In a frequency analysis, the 550 Hz input signal was detected by both the microphone and the DIPS and resulted in a 30 dB level difference therebetween. This indicates that most of the noise input was reduced by the tire wall. The transfer function of the two sensors was converted to a sound transmission ratio into the tire wall $P_{tire}/P_{dir}$, where $P_{dir}$ is with respect to the directional microphone.

Results were also analyzed for a broad input frequency range. The final results of sound transmission ratios versus frequency from 50 to 2000 Hz are shown in FIG. 4.

As depicted in FIG. 4, a region with increased noise transmission was found from 900 to 1600 Hz, which is likely due to the natural resonance of the tire system. As a consequence, this region would not be the ideal working frequency band of the DTPS absent use of some other technique for reducing the response to external acoustic input. Even still, over the majority of this frequency range, the transfer ratio is below 1.0, meaning the DIPS outperforms the external directional microphone in terms of external noise sensitivity.

In the frequency bands below 900 Hz and above 1600 Hz, the transfer ratio of the DIPS to directional microphone response is less than 0.1, indicating that the tire wall blocks more than 90% of undesired environmental noise.

However, as noted above, the resonant response of the tire system can be significantly improved through the use of, for example, acoustic damping foam as is depicted in FIGS. 16 and 17. Thus, once damping material is installed in the respective tire, the sound transmission ratio $P_{tire}/P_{dir}$ is significantly lower in the 900 to 1600 Hz range as compared to the case without such material.

A test was conducted to determine whether DIPS acts as a ground vibration amplifier by sensing, inside the tire using the DIPS, the ground motion or surface wave. The test configuration of FIG. 5 was used, along with a hammer strike approximately one meter distant. A frequency analysis of the DIPS 98 and directional microphone 96 reveals that the DIPS has a high signal to noise ratio in the range about 1000 Hz. This is believed to be related to the natural resonance of the tire system. The transfer function is displayed in FIG. 6. Compared to the directional microphone, the DIPS amplifies the region from 200 Hz to 2000 Hz.

Thus, with respect to equation (2), the tire interior pressure $P_{int}$ is comprised of a very small contribution due to external noise and a relatively large contribution due to ground motion/acceleration. This performance is obviously improved even further upon the introduction of sound damping material into the DIPS-mounted tire.

Another iteration using the same test configuration described above with respect to FIG. 2 was also performed, but with the input source provided by a tire instead of a hammer. This was achieved by jacking up the vehicle and releasing it, thereby generating a low frequency impact. Yet another test was performed by putting a gasoline powered generator (Honda EU2000i) inside the test van close to the test tire, thereby generating high frequency, repeating impact.

FIG. 7 illustrates the response of the four sensors of FIG. 2 (axle-mounted accelerometer 40, DIPS 38, directional microphone 36, and ground-mounted accelerometer 34) in both the time and frequency domains to the low frequency input. FIG. 8 illustrates the response of the same four sensors in both the time and frequency domains to the high frequency vehicle input.

In FIG. 7, frequency peaks at 7 Hz and 14 Hz are found for all four sensors. The transfer functions for the different sensors are calculated as follows: 1) average transfer ratio $T_1 = A_{ground}/A_{axle} = 0.002$; 2) average transfer ratio $T_2 = P_{tire}/A_{axle} = 180$ (Pa/g), where $A_{ground}$ is the ground acceleration, $A_{axle}$ is the axle acceleration, and $P_{tire}$ is the dynamic pressure change.

In FIG. 8, frequency peaks at 35 Hz and 70 Hz are shown for three sensors (axle-mounted accelerometer, DTPS, and directional microphone), but not the ground-mounted accelerometer. This is likely related to the lower impact amplitude of the high frequency input. The transfer functions for the different sensors are calculated as follows: 1) average transfer ratio $T_1 = A_{ground}/A_{axle} = 0.001$; and 2) average transfer ratio $T_2 = P_{tire}/A_{axle} = 1000$ (Pa/g).

From the results of transfer functions of these two tests, low $T_1$ indicates that axle acceleration (tire drop) doesn't excite much ground vibration, which is less than 0.2%. Moreover, high $T_2$ confirm that the DIPS responds directly to axle vibration without picking up lots of environmental noise.

Again with respect to the test configuration shown in FIG. 5, a test was performed to derive an average transfer function between the response of the ground-mounted accelerometer ($A_{ground}$) and the DIPS for the purpose of enabling the determination of ground acceleration from DIPS data. Tests were performed with a 0.25 lb hammer strike, a 1.0 lb hammer strike, and a 4.0 lb hammer strike, each approximately one meter from the accelerometer 90 and DIPS 98. A transfer function G was used for different impact forces.

A cubic spline was used on the data from the plural impacts after applying the transfer function G. After smoothing, the random reconstructed $A_{ground}$ values for the different impacts (0.25 lb, 1.0 lb, 4.0 lb) are shown in FIG. 9. Since the most useful information is found within 5 ms of the ground acceleration signal, a very good prediction of the actual ground acceleration is achieved. Since the acoustic radiation from the surface wave is significantly stronger than acoustic noise, subsurface information can be achieved without the need for a ground-mounted accelerometer.

According to Boyle's Law, assuming the temperature of a system does not change, $PV^\gamma =$ constant, where P is pressure, V is volume, and $\gamma$ is specific heat (equal to 1.4 in air). Thus, $$P_O V_O^\gamma = P_m V_m^\gamma$$

$$P_O V_O^\gamma = P_m (V_O + \Delta V)^\gamma$$

$$P_m = P_O (V_O/(V_O + \Delta V))^\gamma \quad (3)$$

Since $\Delta V = Ad$ where A is the tire footprint area on the road surface and d is the vertical displacement due to ground acceleration, which can be computed from the measured acceleration from the ground-mounted accelerometer, one can plot $P_m$ as a measure of ground acceleration $A_g$.

The use of a Dynamic Tire Pressure Sensor (DIPS) to detect surface and subsurface features of a roadway is similar to impedance measurement in a multi-layered fluid system, which follows the following equation:

$$Z = \frac{P}{v}, \quad (4)$$

where P is the applied pressure at the point of contact between the road and the tire, or approximately 0.25 times the vehicle loading (N) divided by the tire to road contact area ($P_a$), and v is velocity at the road contact point. Z thus contains information about subsurface properties.

The road profile h can be viewed as comprising two components, a lower frequency component $h_1$ attributable to gradual changes in the road geometry, and a higher frequency component h' attributable to ground vibration due to subsurface defects. Thus, the desired higher frequency component h' may be found by low-pass filtering the total profile, or $$h' = h - h_1 \quad (5)$$

It is known that the velocity at the road point of contact is equivalent to:

$$v = h'(t) \quad (6)$$

P thus results from different vertical velocities which can be measured from the dynamic pressure and road acceleration/vibration of the tire body. In such way, potentially damaged subsurface areas can be indirectly revealed through pressure monitoring without the complexity of directly sensing different subsurface layers. Therefore, acoustic impedance of subsurface layers can be obtained by the use of DTPS with respect to the road surface.

A test was performed to determine whether wireless DTPS acts as a pavement condition detector with good sensitivity. The percentage probability of pavement defects and thus the ability to distinguish good and bad road conditions was determined. Data from the DIPS was analyzed over a variety of pavement types, including asphalt-based pavement and concrete pavement.

FIG. 10 provides a flow chart for the data analysis of the DIPS system. An optimized MATLAB program was used to analyze signals from the test system. Specifically, the wireless DIPS and associated circuitry were installed 60 with respect to a vehicle tire, as described above with respect to FIG. 3. The test vehicle was driven 62 at a speed of between 10 to 60 mph over various road conditions, each having respective surface conditions. For each section of roadway, data from the DIPS was gathered 64 at a 30 KHz sampling rate. (For analysis at 1500 Hz, a minimum sampling rate should be ten times the analysis rate, or 15 KHz.) Once wirelessly transmitted to the onboard computer, data analysis 66 was performed with a focus on data in the 2000 Hz frequency range (though useful data may be found throughout the 0 Hz to 20 KHz range). Defect probabilities were thus calculated 68, based fundamentally on the resulting pressure profile.

In an alternative embodiment, sampling rates up to 200 Khz are enabled through a wired connection between the DIPS and the analysis equipment, as discussed below.

The DIPS system was tested on a test van on road sections with different features at speeds of 10 to 60 mph. Images of the road surface conditions were taken during the test with the resolution of one-half meter. Comparisons of six road sections with ascending pothole densities are shown in FIG. 11. Results show tire pressure changes over 0.15 psi (1000 Pa) but usually less than 1.0 psi (6894 Pa) for most surface defects. Different road features, such as potholes, manholes, joints and rail tracks, were distinguished using frequency analysis within a frequency range from 0 to 2000 Hz. The data could be analyzed onboard in real-time by auto window selection every second, or post-analysis by manual window selection.

To obtain a better understanding of the response to different road features, frequency analysis of the DIPS results were carried out and the results are shown in FIG. 12. In graph No. 1, clear peaks at 200 Hz are due to tire cavity resonance and those at 400 Hz and 600 Hz are the harmonics of those at 200 Hz. Peaks observed around 1200 Hz are likely related to the tire tread impact with the road and may result from the amplified ground vibration that was demonstrated above and with respect to FIG. 6.

In the frequency domain, the most useful information for establishing DIPS utility is at lower frequencies, such as below 400 Hz. As noted, the peak at 200 Hz comes from the tire resonance frequency, and the amplitude may be used to distinguish different roadway surface features. In graph No. 2 of FIG. 12, there is an ascending trend of energy with road defect levels for both the peak at 200 Hz and in the frequency range of 30 Hz to 15 kHz. The most useful range was 0 to 400 Hz. The trend was present in other tests and studies of different road surfaces and the results are shown in FIG. 13. The acoustic resonance peak at 200 Hz emphasizes the benefit achieved with the use of acoustic damping material within the tire, such as the foam material discussed above.

In FIG. 13, the linear trend of different defect heights is observed. This indicates that the most useful information about road features is near or in the range of 0 to 400 Hz and both the amplitude of the 200 Hz peak and the energy over 0 to 400 Hz can be used to characterize possible defects of the road surface. Thus good and bad road conditions can be identified.

In an alternative embodiment to the wireless DIPS described in the foregoing, a connection structure was designed and fabricated to enable a wired connection between the DIPS and an on-vehicle data processing system. The wired connection allows for higher sampling rates, for example 200 KHz, and synchronization of the DTPS with other sensors. In various embodiments, the test vehicle may be equipped with one or more of a body-mounted accelerometer, an axle-mounted accelerometer, a directional microphone in front of the DIPS-instrumented tire, and a directional microphone behind the DIPS-instrumented tire. Each of these sensors provides input to the onboard data processing system.

In FIG. 14, the graph illustrates that the Signal to Noise Ratio (SNR) for DIPS is higher than either of the directional microphones mounted in front of or behind the DIPS-mounted wheel. In particular, within the 0 to 800 Hz range, the SNR of DIPS is approximately ten times (20 db) higher than that either of the directional microphones.

In FIG. 15, the graph provides normalized values for the acceleration and pressure measured by the axle-mounted accelerometer and the DIPS, respectively. Notably, DIPS data aligns very well with the axle-mounted accelerometer data.

A test was performed to determine whether the DIPS data could be used to represent a road surface profile. Axle-mounted accelerometer data alone may not be used to reliably characterize a road surface profile due to vehicle-induced accelerations. Assuming a linear relationship between road surface height and tire pressure, a transfer function G(w) can be calculated from empirical studies. From that, a road height profile h(x(t)) can be computed for an unknown road section using G(w).

The test included driving over a bar of a known geometry, dynamically measuring the tire pressure (p), and calculating the transfer function G(w).

$$p(t) = \int_{-\infty}^{\infty} h(\tau)g(t-\tau)\,d\tau \qquad (7)$$

A Fast Fourier Transform (FFT) is performed to achieve:

$$P(w) = H(w)G(w) \qquad (8)$$

For an unknown road, given P' and the derived transfer function G, the goal is to find the roadway height h' using an inverse FFT.

The pressure input from the DTPS includes a component contributed by the vehicle acceleration.

$$p_{tire}(t) = p_{axle} + P_{road} \qquad (9)$$

In FIG. 18, the first two peaks in the left-hand graph of DTPS pressure reflect the vehicle tire hitting a 2.5 inch wooden block. The first peak is due to vertical road surface acceleration. The second peak is due to acceleration of the vehicle axle.

A test was performed to identify the contribution of axle acceleration to tire pressure changes. A vertical acceleration was applied to the stationary test vehicle and the tire pressure $P_{axle}$ and axle acceleration $A_{axle}$ were measured. The transfer function was then calculated:

$$G'(w) = P_{axle}(w)/A(w) \qquad (10)$$

During a driving test, axle acceleration A'(w) was measured and, using the previously determined transfer function, the tire pressure attributable to axle acceleration was calculated:

$$P_{axle}'(w) = G'(w)A'(w) \qquad (11)$$

The calculated value for $P_{axle}'(t)$ is then subtracted from the DTPS-measured tire pressure $P_{tire}'(t)$. The road surface height profile was then calculated using the inverse FFT method described above.

The graph of FIG. 15 illustrates the DTPS-measured tire pressure and the contribution due to axle acceleration.

In FIG. 19, the graph on the left provides road height profiles for both relatively smooth and rough roads. The graph on the right provides the corresponding Weibull distribution for the same roads. The results show that the road height is more than 1 cm for rough road sections, and 0.2 cm for the smooth road section. The different road sections are distinguishable in both the reconstructed height profiles and well as the Weibull distributions. It is estimated that there is roughly a 0.1 cm error in the reconstructed road height profile and that there is a linear resolution of a surface feature of approximately 5 to 10 cm in width at speeds of 10 to 60 mph. Such a profile can then be used to estimate the International Roughness Index (IRI) of the roadway, the Mean Texture Depth (MTD), defects, potholes, etc.

The foregoing tire-mounted DIPS sensor system obviously requires a source of electrical energy. As previously noted, conventional batteries, as commonly used in Tire Pressure Management Systems (TPMS), have a limited useful life, thus requiring recharge or replacement. As an alternative, the following describes a mechanical energy harvesting system and method that is easily adapted for supplying electrical power to the DTPS system.

Magnetostatic potential energy is produced by magnetic coupling between a hard magnet 76 and a solenoid or coil 74. This type of energy is linear with respect to the oscillation frequency of the coupling or relative motion between the components. As shown in FIG. 20, a magnet array 70 is arranged with the magnetization of the magnets 76 antiparallel to each other in a semicircular, arcuate magnet holder or fixture 72. A spatially heterogeneous magnetic field exists above each magnet pair. When a rotating solenoid 74 is present above the magnet array, a maximized flux change will be induced with the magnetization in the core of the solenoid reversed by 180°. This flux change results in an induced voltage in the coil with the frequency related to the rotational speed of the magnet array and the number of the magnets.

According to Faraday's Law, the induced voltage in the coil is $$V_{open} = \frac{d\varphi(t)}{dt} = \frac{d\int \mu_0\{H[x,y(x)] + M[x,y(x,t)]\}A\,dN}{dt}, \qquad (12)$$

$$= \frac{d\int \mu_0 M[x,y(x,t)]\}A\,dN}{dt} \qquad (13)$$

where M is the magnetization in the core, $\mu_0$ is the permeability constant, A is the cross-sectional area of the core, dN is the number of loops in the infinitesimal length unit of the coil, and $$dN = \frac{N_L}{d_w}d_x, \qquad (14)$$

where $N_L$ is the number of loop layers in the coil and $d_W$ is the copper wire diameter. When a load resistance $R_{load} = R_{coil}$ is connected across the solenoid, the maximum output power is $$P_{max} = \frac{(V_{open}/2)^2}{R_{coil}} = \frac{4S}{R_{coil}}\left(A'\pi\frac{N_L}{d_w}\right)^2\left(\int_0^L \left\{\frac{dM[x,y(x,t)]}{dt}\right\}dx\right)^2. \qquad (15)$$

Equation 15 indicates that the output power depends on the change rate of magnetization in the core of the solenoid. Moreover, at a particular frequency, the output power depends on the total magnetic flux change in the solenoid, which in turn relates to the permeability of the magnetic core.

The following describes an experimental configuration used to validate the presently disclosed concepts. A soft magnetic material such as produced by the MuShield Company was used as core material for the solenoid. The solenoid was configured as shown in FIG. 21 with dimensions of 1 cm by 1.1 cm by 2.2 cm (2.42 cm³), a total of 250 turns and a resistivity of 4.5Ω. Multi-layered (>10) core materials were used to further increase the permeability (>10,000) of the solenoid.

NdFeB N45SH Neodymium cylindrical hard magnets (such as available from MMC Magnetic, Ltd.) with dimensions of 2.5 cm by 2.5 cm by 2.5 cm were used. The maximum energy product $(BH)_{max}$ is 43-46 MgOe. The magnetization orientation is through the axis of the cylinder. The magnetic holder is made from an aluminum sheet of Alloy 6061 and screwed into the brake dust shield of a Chevrolet Express 3500 cargo van. The semicircular, arcuate hard magnet array is configured to avoid the disc brake caliper. FIG. 22 shows the fabricated magnet array holder disposed on the brake dust shield of the wheel.

For validation purposes, a tire rotation stand was built for an energy harvester prototype with an end part of a Chevrolet Express 3500 cargo van axle and wheel, a 10 horsepower electrical motor to rotate the wheel, and a 3:1 gear reducer. The maximum wheel rotating speed is equivalent to approximately 60 mph. The van end part is fabricated with a brake dust shield from the actual vehicle.

The distance between the solenoid and the magnet array is within 2 cm. When the tire is rotating, the relative motion between the solenoid and the stationary hard magnet array leads to maximized flux change and induced voltage. The measurement electronics are shown in FIG. 23, and include a rectifying circuit 80, a voltage conversion circuit (as required) 82 providing a DC power output to, for example, the DIPS, a wireless transmission sensor board 84 (Waspmote with 802.15.4 ZigBee network), and a battery with associated charging circuit 86. The instrumented box was assembled inside the center cap of the van wheel. In addition, the solenoid and the sensor were balanced to avoid interference with the tire rotation. The data was read from a laptop using a complimentary ZigBee receiver.

The field strength of the hard magnets was tested in the lab through the use of the wireless transmitter to provide references for the energy harvester prototype. The magnetic field is 150 Gauss at 4 cm away, along its magnetization orientation through the height of the cylinder. By fixing the solenoid within 2 cm from the magnets, maximum flux inside the solenoid core can be achieved and the magnetic field is more than 5 times higher than that of the 4 cm distant configuration. The maximum power density is 5 W/cm³. Greater energy recovery is achieved by providing a circular array of solenoids, each connected to a rectify circuit, preferably centrally located with respect to the wheel for balance purposes. Such an array may be either affixed directly to a vehicle wheel surface or to a fixture that is itself affixed to the wheel.

The energy harvester was demonstrated on the tire rotating stand at a speed from 10 to 60 miles/hr. With the wireless measuring system, voltage data could be read with a sampling rate of 200 Hz. There was determined to be a linear relationship between the rotational speed and the final output power. As the rotational speed (working frequency of the energy harvester) increases, the power also increases. The best result is shown in FIG. 24 with the speed of 60 mph (26.8 m/s) where power density is around 4.5 W/cm³. Results at a speed of 40 mph are also shown in the same graph along with a comparison of a commercially available power choke (PCH) (Coilcraft, PCH-45-476LT) at 60 mph. The fabricated solenoid with high permeability core did show a clear improvement in the output voltage as compared to the PCH. DC voltage, derived from an onboard AC to DC converter, provides approximately 3.4 V. The higher voltage is stored to an onboard rechargeable battery 86 for additional energy storage in case of higher power consumption. The battery ideally is capable of thousands of recharge cycles. The generated power is also sufficient to power an onboard temperature sensor and position sensor (not shown). An associated charging circuit and power manager with charge control (not shown) are also provided in a first embodiment.

The disclosed energy harvester can be adapted to power wireless vehicle-mounted sensors and associated circuitry, other than DTPS, that otherwise need a battery for a consistent power supply. For example, the energy harvester has been adapted for powering a real-time TPMS. However, DIPS monitoring can enable road monitoring and inspection in real time or near-real time. In such cases, dynamic tire pressure is measured instead of static pressure. A higher sampling rate is required as well as a higher transmission rate for this application. For example, a sensor node requires around 25-50 mA during a transmit/receive operation, and only a few μA during sleep mode. The system requires sampling data once every millisecond, and transmitting a data package of 100 samples every 0.1 s. Operating time for transmitting or receiving in such a sensor node is approximately 0.1 s, depending on the distance of communication and the noise present in the environment. The transmit/receive load requirement of the sensor node is 35 mA for a typical distance of 200 m and the sleep mode requirement is 75 μA. The sensor main board consumes an average of 9 mAh. The active mode energy requirement per hour is thus $$P_a = 60 \times 60 \times 10 \times \left[35 \text{ mA} \times \frac{0.1}{60 \times 60} \text{hrs}\right] + 9 \text{ mAh} = 45 \text{ mAh}. \quad (16)$$

Sleep mode energy requirement per hour is $$P_s \approx 1/\text{hrs} \times 75 \text{ μW} = 75 \text{ μAh}. \quad (17)$$

Total energy requirement per hour is 45 mAh. Therefore, the number of hours that a 3.3 V Li battery would last is $$t \approx \frac{500 \text{ mAh}}{45 \text{ maAh}} = 11.1 \text{ hours}. \quad (18)$$

For real-time dynamic tire pressure monitoring, which requires data collection at a high sampling rate (>1000 samples/second), the system requires 45 mAh of energy per hour for both active mode and sleep mode with a sampling rate at 1000 data points/sec. The energy harvester provides around 500 mAh when the car drives at 60 mph and 300 mAh when the car drives at 40 mph. With the capacity of an onboard rechargeable battery, the energy harvester system can be customized to the downtime of the vehicle. For example, using the same battery, the system can be in sleep mode for more than thousands of hours. Therefore this approach has the potential to overcome the battery limitation of the existing TPMS approaches, and it is able to provide sufficient power for the real-time tire pressure sensor at different modes.

The various embodiments and parameters described above are to be viewed as exemplary and not limiting, and alternatives may be employed. For example, while the DIPS employed in the foregoing tests was a PCB Piezotronics Model 106B52 sensor, any suitable sensor may be employed. The DIPS is depicted as being mounted on to a tire valve stem. However, a "T" connection may also be used to couple the sensor to the valve stem while at the same time enabling a source of pressurized air to be coupled to the valve stem.

The foregoing embodiments focused on the use of the DIPS and associated electronics with respect to one tire/wheel of a vehicle. However, multiple such DIPS implementations may be used on a single vehicle to achieve an array of sensors, thereby enabling an assessment, performed by the onboard data processor, of the coherence of the respective measurements.

In a further embodiment, a static tire pressure sensor may be used, though sampled at a rate faster than that used with commercially available IMPS.

While the primary use of DIPS has been described in the context of roadway surface and subsurface characterization, it may also find utility in tire design characterization. For example, a vehicle fitted with a DIPS-instrumented tire may be driven over a test roadway and the pressure response recorded. A comparison may then be made to other tire designs that were driven over the same test roadway to assess how different designs respond to roadway variations. The different design aspects may include belt material, belt configuration, tire material, tread design, etc.

In addition to finding utility for surface and subsurface characterization, the DIPS system may also be used to detect road surface conditions such as excessive standing water, ice, or sand/gravel. A DIPS-instrumented tire can be driven over such roadway conditions in a controlled experiment to derive reference profiles for internal tire pressure. Upon detection of a pressure profile characteristic of such conditions, the onboard processor, which may be configured as part of the standard vehicle control processing system, may issue an audible or visual warning to the vehicle operator. Such a function may require detection of such a pressure profile for a minimum period of time, and may require input from other vehicle-based or networked sensors, including humidity and/or temperature sensors.

The acoustic damping material has been described in the foregoing as provided in sheet form, with pyramidal projections. Any suitable material or form factor may be employed, however. For example, sound damping material may be integrated into the tire during manufacturing. Alternatively, the acoustic damping material may be applied to the interior of the tire by spraying.

Further, while the disclosed approach has been to include a passive material inside a tire, an active sound cancelling approach may also be employed, in which externally induced noise may be measured within the tire using a microphone connected, wired or wirelessly, to a data processing device, which may then cause noise canceling tones to be introduced through a suitable transducer, such as a speaker, disposed on or in the tire.

While not depicted in the drawings, a geopositioning device such as a Global Positioning System (GPS) receiver may be integrated into the disclosed system. Data from the DIPS may be time-stamped according to the time stamp of the GPS data. Thus, roadway condition information can be mapped with precision. Still images and/or video of the roadway and/or immediate environment may also be time-stamped, associated with or integrated into the processed DIPS data to enable the later location of any pavement portions requiring maintenance. The capture f such still image or video data may be continuous or initiated upon detection of roadway abnormalities.

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What is claimed is:

1. A system disposed in a vehicle for measuring surface height profile of the roadway over a range of driving speeds, comprising:
   a dynamic tire pressure sensor coupled to a valve stem of a first tire of the vehicle for dynamically measuring tire pressure changes caused by the interaction of the respective tire and the roadway while the vehicle is moving on the roadway;
   a signal processing circuitry, centrally disposed on a first wheel of the vehicle, the first tire being mounted on the first wheel and the signal processing circuitry having electrical communication with the pressure sensor for receiving input of the dynamic tire pressure data from the dynamic tire pressure sensor and producing an output of the processed tire pressure data; and
   a signal recovery and processing computer having an associated database, the computer disposed with the vehicle for receiving the processed tire pressure data from the signal processing circuitry, for providing an output of the surface height profile of the roadway on which the vehicle is traveling, and for storing the analyzed data in the database.

2. The system according to claim 1, further comprising a wireless data transmitter, disposed in conjunction with and in electrical communication with the signal processing circuitry for receiving processed dynamic tire pressure data therefrom, and a wireless receiver, disposed in conjunction with the signal recovery and processing computer, whereby the transmitter is for wirelessly transmitting the processed tire pressure data to the receiver.

3. The system according to claim 1, wherein the signal processing circuitry is coupled to the computer via a slip ring and electrical signal cabling.

4. The system according to claim 3, wherein signal processing circuitry is capable of a higher sampling rate when connected to the signal recovery and processing computer via a slip ring than via a wireless transmitter and receiver pair.

5. The system according to claim 1, wherein the signal processing circuitry comprises an amplifier and an analog-to-digital converter.

6. The system according to claim 1 further comprising an energy harvester, disposed in conjunction with the first wheel, for providing electrical power to the pressure sensor and signal processing circuitry, the energy harvester comprising an arcuate array of magnets fixedly disposed adjacent the first wheel, at least one solenoid disposed in conjunction with the first wheel for rotation therewith, and a rectifier circuit for rectifying the alternating current generated in the at least one solenoid by the array of magnets.

7. The system according to claim 6, wherein the energy harvester further comprises a voltage conversion circuit, for adjusting the voltage from the rectifier circuit, and a battery for storing excess power generated in the at least one solenoid.

8. The system according to claim 1, further comprising a geopositioning device in communication with the computer for enabling the computer to associate location data with the analyzed data.

9. The system according to claim 1, further comprising at least one of a still and video camera in communication with the computer for enabling the computer to selectively associate image data with the analyzed data.

10. The system according to claim 1, further comprising an accelerometer disposed on an axle associated with the first wheel, the accelerometer in communication with the computer for enabling the computer to remove the effects of vehicle body accelerations from the analyzed data from the dynamic tire pressure sensor.

11. The system according to claim 1, further comprising threshold data stored in association with the computer for enabling the computer to identify inferior roadway conditions from the analyzed data.

12. The system according to claim 11, wherein the computer is configured to respond to the analyzed data attaining at least one threshold by at least one of highlighting the respective analyzed data in the database, sending an alert to an operator, and wirelessly transmitting the analyzed data to a remote database.

13. The system according to claim 12, wherein the alert is selected from the group consisting of an audible or visual indication to personnel in the vehicle, an electronic communication to remote personnel, and an electronic communication to a remote computer.

14. The system according to claim 11, wherein the analyzed data attaining at least one threshold is indicative of the presence of a roadway defect.

15. The system according to claim 1, further comprising acoustic damping material disposed in the first tire for reducing the resonant frequency response associated therewith.

16. The system according to claim 15, wherein the damping material is a sheet of acoustic damping foam with pyramidal projections.

17. The system according to claim 1, wherein the pressure sensor is coupled to the valve stem via a T connector, thereby enabling compressed air to be selectively introduced into the first tire without requiring the pressure sensor to be removed.

18. The system according to claim 1, wherein the signal processing circuitry and data transmitter are centrally disposed in a hub cover mounted on the first wheel.

19. The system according to claim 1, wherein the dynamic tire pressure sensor and signal processing circuitry form a tire pressure data source, and wherein the system further comprises a second such tire pressure data source in association with a second tire of the vehicle, both of which are in communication with the signal recovery and processing computer, thereby forming a tire pressure data source array.

20. The system according to claim 1, further comprising an accelerometer mounted on the axle proximate the first tire and first wheel and in communication with the signal recovery and processing computer, wherein the signal recovery and processing computer removes the vertical vehicle acceleration detected by the axle-mounted accelerometer from the received tire pressure data in order to characterize the roadway surface height profile.

21. The system according to claim 20, wherein the characterized roadway surface height profile is selected from the group consisting of an estimated International Roughness Index value, a Mean Texture Depth value, cracks, potholes, expansion joint, bleed, and corrugation.

22. The system according to claim 1, wherein the signal recovery and processing computer analyzes the received data by using a transfer function based upon a predetermined relationship between ground vibration and dynamic tire pressure, whereby an estimate of actual ground vibration, and thus subsurface condition, is derived from the analyzed tire pressure data.

23. The system of claim 1, wherein the roadway has a known profile, and wherein the characterization of the roadway realized by the signal recovery and processing computer is compared to the known profile to derive an assessment of the ride comfort performance of the respective tire.

24. The system according to claim 1, wherein characterization of the roadway includes an estimate of relative motion between the respective tire and the roadway, such relative motion being interpretable as indicative of a substance between the respective tire and the roadway, the substance being selected from the group consisting of ice, water, and particulate material.

25. A method of determining a road height profile, comprising:
dynamically detecting the internal pressure of a first vehicle tire using a dynamic tire pressure sensor disposed in conjunction therewith while the vehicle is traveling on a portion of a roadway;
sampling the tire pressure data using an on-wheel sampling and signal conditioning circuit;
providing the sampled tire pressure data to a processing device disposed within the vehicle;
generating pressure profile data by an on-vehicle processing device from the sampled tire pressure data;
measuring the acceleration of an axle due to the vehicle traveling on the portion of the roadway using an axle-mounted accelerometer disposed proximate the first vehicle tire;
applying, by the processing device, a predetermined transfer function to derive axle pressure from measured axle acceleration;
removing the effect of vehicle-induced accelerations by subtracting the axle pressure from the sampled tire pressure and forming a resulting pressure profile therefrom; and performing a frequency analysis of the pressure profile, by the processing device, to generate an estimate of road height profile.

26. The method of claim 25, further comprising the step of low-pass filtering, by the processing device, the frequency analysis results to remove road geometry features therefrom.

27. The method of claim 25, wherein the step of providing comprises wirelessly transmitting the sampled tire pressure data from the sampling and signal conditioning circuit to the processing device.

28. The method of claim 25, wherein the step of providing comprises providing the sampled tire pressure data to the processing device via a slip-ring and electrical conductors.

* * * * *